US008087980B2

(12) United States Patent
Palmer

(10) Patent No.: US 8,087,980 B2
(45) Date of Patent: Jan. 3, 2012

(54) POSITIVE AIR PRESSURE ISOLATION SYSTEM

(75) Inventor: David W. Palmer, Andover, MA (US)

(73) Assignee: American Innovative Research Corp., Andover, MA (US)

( * ) Notice: Subject to any disclaimer, the term of this patent is extended or adjusted under 35 U.S.C. 154(b) by 88 days.

(21) Appl. No.: 12/603,107

(22) Filed: Oct. 21, 2009

(65) Prior Publication Data

US 2010/0041328 A1 Feb. 18, 2010

Related U.S. Application Data

(63) Continuation of application No. 11/805,776, filed on May 24, 2007, now Pat. No. 7,625,277.

(60) Provisional application No. 60/802,977, filed on May 24, 2006.

(51) Int. Cl.
*F24F 7/00* (2006.01)
*B01D 50/00* (2006.01)

(52) U.S. Cl. ...................................... 454/255; 55/385.2

(58) Field of Classification Search .................. 454/255; 55/385.2

See application file for complete search history.

(56) References Cited

U.S. PATENT DOCUMENTS

| 2,904,242 | A | 9/1959 | Pearson | 230/69 |
|---|---|---|---|---|
| 3,128,378 | A | 4/1964 | Allen et al. | 250/43 |
| 3,403,252 | A | 9/1968 | Nagy | 250/46 |
| 3,518,046 | A | 6/1970 | Cicirello | 21/53 |
| 3,757,495 | A | 9/1973 | Sievers | 55/279 |
| 3,798,879 | A | 3/1974 | Schmidt-Burbach et al. | 55/102 |
| 3,975,790 | A | 8/1976 | Patterson | 15/339 |
| 3,990,069 | A | 11/1976 | Schuman | 340/240 |
| 4,786,812 | A | 11/1988 | Humphreys | 250/455.1 |
| 4,905,579 | A | 3/1990 | Dame | 98/1.5 |

(Continued)

FOREIGN PATENT DOCUMENTS

GB 2 110 815 6/1983

(Continued)

OTHER PUBLICATIONS

European Patent Office, International Search Report and Written Opinion of the International Searching Authority—Application No. PCT/US2007/012585, dated Oct. 26, 2007 (16 pages).

(Continued)

*Primary Examiner* — Steven B McAllister
*Assistant Examiner* — Helena Kosanovic
(74) *Attorney, Agent, or Firm* — Sunstein Kann Murphy & Timbers LLP

(57) ABSTRACT

An air-pressure-control system, the system comprising a system inlet, a system outlet, and a variable-speed fan configured to operate at a speed. A motor controller in communication with the fan is configured to control the speed of the fan. A differential-pressure transducer configured to monitor an air pressure at the system inlet and an air pressure at the system outlet. A closed-loop pressure controller in communication with the motor controller and differential-pressure transducer, wherein the pressure controller is configured to vary the speed of the fan based on the pressure differential between the inlet and outlet of the system, thereby controlling a pressure within a space. An ultraviolet kill chamber may be disposed between the inlet and outlet to expose airborne particulate to UV radiation. The system may also have a filter located within an air-flow path between the system inlet and system outlet.

117 Claims, 12 Drawing Sheets

U.S. PATENT DOCUMENTS

| | | | |
|---|---|---|---|
| 5,074,894 A | 12/1991 | Nelson | 55/210 |
| 5,152,814 A | 10/1992 | Nelson | 55/270 |
| 5,225,167 A | 7/1993 | Wetzel | 422/121 |
| 5,257,736 A | 11/1993 | Roy | 236/49.3 |
| 5,330,722 A | 7/1994 | Pick et al. | 422/121 |
| 5,360,469 A * | 11/1994 | Baron et al. | 95/273 |
| 5,399,319 A | 3/1995 | Schoenberger et al. | 422/121 |
| 5,523,057 A | 6/1996 | Mazzilli | 422/121 |
| 5,525,107 A | 6/1996 | Shao | 454/204 |
| 5,533,305 A | 7/1996 | Bielecki | 52/79.1 |
| 5,538,471 A | 7/1996 | Guiles, Jr. | 454/238 |
| 5,612,001 A | 3/1997 | Matschke | 422/121 |
| 5,616,172 A | 4/1997 | Tuckerman et al. | 96/16 |
| 5,635,133 A | 6/1997 | Glazman | 422/24 |
| 5,664,995 A | 9/1997 | O'Keefe | 454/58 |
| 5,761,908 A | 6/1998 | Oas et al. | 62/3.2 |
| 5,835,840 A | 11/1998 | Goswami | 422/186.3 |
| 5,837,040 A | 11/1998 | Caughron et al. | 96/224 |
| 5,837,207 A | 11/1998 | Summers | 422/121 |
| 5,884,500 A | 3/1999 | Wetzel | 62/259.1 |
| 5,987,908 A | 11/1999 | Wetzel | 62/259.1 |
| 5,997,619 A | 12/1999 | Knuth et al. | 96/224 |
| 6,022,511 A | 2/2000 | Matschke | 422/121 |
| 6,062,977 A | 5/2000 | Hague | 454/341 |
| 6,079,627 A * | 6/2000 | Kettler | 236/49.3 |
| 6,213,117 B1 * | 4/2001 | Kirk et al. | 126/285 R |
| 6,221,314 B1 | 4/2001 | Bigelow | 422/24 |
| 6,228,327 B1 | 5/2001 | Matschke | 422/121 |
| 6,264,888 B1 | 7/2001 | Palestro et al. | 422/24 |
| 6,383,241 B1 | 5/2002 | Janus et al. | 55/385.2 |
| 6,438,971 B1 | 8/2002 | Lentz et al. | 62/78 |
| 6,464,760 B1 | 10/2002 | Sham et al. | 96/117.5 |
| 6,497,840 B1 | 12/2002 | Palestro et al. | 422/24 |
| 6,500,387 B1 | 12/2002 | Bigelow | 422/24 |
| 6,716,406 B2 | 4/2004 | Reisfeld et al. | 423/245.1 |
| 6,783,578 B2 | 8/2004 | Tillman, Jr. | 96/224 |
| 6,818,035 B2 | 11/2004 | McGahey, Jr. | 55/385.1 |
| 6,849,234 B2 | 2/2005 | Lentz et al. | 422/24 |
| 6,884,399 B2 | 4/2005 | Reisfeld et al. | 422/186.3 |
| 6,962,619 B1 | 11/2005 | DeRosa et al. | 95/267 |
| 2001/0048889 A1 | 12/2001 | Palestro et al. | 422/4 |
| 2002/0020297 A1 | 2/2002 | Harris et al. | 95/273 |
| 2002/0144601 A1 | 10/2002 | Palestro et al. | 95/273 |
| 2003/0101700 A1 | 6/2003 | Burdine et al. | 55/385.2 |
| 2003/0217641 A1 | 11/2003 | Palestro et al. | 95/273 |
| 2004/0041564 A1 | 3/2004 | Brown | 324/318 |
| 2004/0047776 A1 | 3/2004 | Thomsen | 422/186.07 |
| 2004/0175304 A1 | 9/2004 | Reisfeld et al. | 422/186.3 |
| 2005/0027453 A1 * | 2/2005 | Fort et al. | 702/14 |
| 2005/0108996 A1 | 5/2005 | Latham et al. | 55/385.2 |
| 2005/0163648 A1 | 7/2005 | Liang | 422/1 |
| 2005/0211415 A1 | 9/2005 | Arts et al. | 165/59 |
| 2005/0252027 A1 * | 11/2005 | Kolari | 34/513 |
| 2006/0021375 A1 | 2/2006 | Wetzel et al. | 62/419 |
| 2006/0057020 A1 | 3/2006 | Tufo | 422/24 |
| 2006/0177356 A1 | 8/2006 | Miller | 422/121 |

FOREIGN PATENT DOCUMENTS

| | | |
|---|---|---|
| JP | 2003-240260 | 8/2003 |
| WO | WO 94/08633 | 4/1994 |
| WO | WO 01/61252 | 8/2001 |
| WO | WO 2005/039659 | 5/2005 |

OTHER PUBLICATIONS

The International Bureau of WIPO, International Preliminary Report on Patentability—Application No. PCT/US2007/012585, dated Nov. 28, 2008 (9 pages).

* cited by examiner

POSITIVE AIR PRESSURE ISOLATION SYSTEM

PRIORITY

This application is a continuation of U.S. application Ser. No. 11/805,776, entitled "Positive Air Pressure Isolation System," filed May 24, 2007, and naming David W. Palmer as inventor, the disclosure of which is incorporated herein, in its entirety, by reference.

U.S. application Ser. No. 11/805,776, in turns, claims priority from U.S. provisional application Ser. No. 60/802,977, filed May 24, 2006, entitled "Positive Air Pressure Isolation System,", and naming David W. Palmer as inventor, the disclosure of which is hereby incorporated by reference in its entirety.

FIELD OF THE INVENTION

The invention generally relates to a positive air pressure isolation system. More specifically, the invention relates to the management and cleaning of air flow in or out of a closed space to produce a constant positive (+) or negative (−) room air pressure.

BACKGROUND ART

Air pressure control systems are used in many hospital room and semiconductor clean room applications to create isolation and containment areas. Isolation and containment techniques manage airborne micron size particles and micro organisms such as viruses, bacteria, fungus, mold, spores, and dust. Such techniques add to the health benefits of those living and working in the pressurized room by filling the space with clean air and removing contaminated air. The pressurization of a closed space further prevents the leakage of contaminated air into the room. As a result, the World Health Organization (WHO) recommends the use of isolation and containment rooms as a viable method of slowing the spread of airborne viruses.

The negative air pressure design criteria of many of the prior art control systems capture and contain the air containing micro-organisms and, then, neutralize or destroy the airborne contamination before releasing the air back into the environment. By evacuating air from the room, the leakage of air is into the room, preventing the escape of contamination.

Existing air pressure control systems have been built into containment rooms in hospitals specializing in the treatment of Tuberculosis (TB) and other airborne diseases. The number of such rooms is adequate for today's medical requirements, but will not meet the needs of an out break of a human to human version of the avian influenza (i.e., Bird Flu), or similar airborne disease. If an outbreak appears in a metropolitan area, the number of containment rooms will be inadequate to accommodate the number of inflicted people. Further, if the outbreak occurs in a rural area, hospitals with containment rooms may not be located within a reasonable distance.

Therefore, the challenge is to find a way to make available positive and negative air pressure control systems that will convert a standard room at the site of an outbreak of the influenza. The control systems must be easily installed and made available in sufficient quantities to isolate and protect the first responders; and to contain, capture, and destroy the contaminated air used by symptomatic patients.

SUMMARY OF THE INVENTION

In accordance with an embodiment of the present invention, a system is provided for the control of air pressure in a closed space. The system may be installed through a window and contains a system inlet and system outlet. The system may also contain a variable-speed fan, and a motor controller to control the speed of the fan. The variable-speed fan may be reversible to allow the system to provide a positive or negative pressure in the closed space.

The system may include a differential-air-pressure transducer. The differential-air-pressure transducer monitors the air pressure at the system inlet and system outlet. In some embodiments, the differential-air-pressure transducer may be a hot wire or solid state anemometer. A closed-loop controller, in communication with the motor controller and the differential pressure transducer, can vary the speed of the fan based on the pressure differential between the inlet and outlet of the system, thereby controlling a pressure within a space.

Further, the air-pressure-control system may also include a control panel in communication with the closed-loop controller. The control panel may be capable of receiving setpoint values. Based on the received setpoint values, the control panel may change the speed or the direction of the fan. The control panel may further include a switch that allows a user to select between positive and negative room pressures.

In accordance with further embodiments of the present invention, the closed-loop controller may include a microprocessor. The microprocessor can compare an output from the differential-air-pressure transducer and the setpoint value and adjust the speed or direction of the fan based on the difference between the differential-air-pressure transducer output and the setpoint value.

The air-pressure-control system may also include a safety sensor in communication with the microprocessor. The safety sensor may be configured to alarm when the air pressure control system is not operating at the setpoint values.

In accordance with further embodiments, the air-pressure-control system may also include a germicidal radiation chamber. The germicidal radiation chamber may be located in an airflow path within the air-pressure-control system and may contain at least one UV light source. The germicidal radiation chamber may also include reflective interior surfaces to reflect the UV light produced by the UV light source. Baffles may be located at one or both ends of the germicidal radiation chamber to prevent UV light from exiting the germicidal radiation chamber. The airflow path containing the germicidal radiation chamber may be blackened to prevent UV reflection through the system inlet and outlet. The wavelength of the UV light may be, but is not limited to, 253.7 nanometers. The UV light may pass entirely across a portion of the airflow path.

In an additional embodiment of the present invention, the air-pressure-control system does not contain a filter.

In some embodiments, the air-pressure-control system may contain a second airflow path. The differential-air-pressure transducer may be located within the second airflow path.

In accordance with other embodiments, an air-pressure control system with a filter can control the air pressure within an enclosed space. The system includes a system inlet, a system outlet, and a first filter located within an airflow path between the system inlet and system outlet. The system may also have a variable-speed fan configured to operate at a speed, a motor controller in communication with the fan and configured to control the speed of the fan, and a differential-air-pressure transducer configured to monitor an air pressure at the system inlet and an air pressure at the system outlet. The differential pressure transducer can be a hot-wire or solid state anemometer. A closed-loop controller, in communication with the motor controller and differential-pressure transducer, can vary the speed of the fan based on the pressure differential between the inlet and outlet of the system. By controlling the pressure differential between the inlet and outlet, the system is able to control the pressure within a space.

The fan can be reversible, and the system can include a control panel in communication with the closed-loop controller. The control panel can receive setpoint values and change the speed or a direction of the fan based on the setpoint value. The control panel can include a switch that allows a user to select between positive and negative room air pressures. The system may also include a microprocessor that compares the output from the differential pressure transducer and the setpoint value, and adjusts the speed or direction of the fan based on the difference between the values. A safety sensor in communication with the microprocessor can alarm when the air-pressure-control system is not operating at the setpoint values.

In some embodiments, the system can also include a germicidal radiation chamber located within the airflow path. The germicidal radiation chamber may include at least one UV light source and may have a reflective interior surface that reflects the UV light produced by the UV light source. The germicidal radiation chamber may also have at least one slot providing access to the filter. The first filter may be located at a first end of the germicidal radiation chamber. The system may also include a second filter located at a second end of the germicidal radiation chamber.

The airflow path may be blackened to prevent UV reflection through the system inlet and system outlet. Additionally (or alternatively), the system may have baffles located at an at least one end of the germicidal radiation chamber to prevent UV light from exiting the germicidal radiation chamber. In some embodiments, the UV light has a wavelength of about 253.7 nanometers.

In some embodiments, the air-pressure-control system is configured for through-window installation. The first filter can be a translucent glass fiber filter, and may have a metal frame. The filter may also be pleated and oriented such that the pleats are vertical. The UV lamps can be oriented such that they are transverse to the pleats of the first filter.

The system further may also include an air flow sensor located within the germicidal radiation chamber. The air flow sensor can be mounted on an inside wall of the germicidal radiation chamber. The air flow sensor can be oriented such that it is co-linear with the flow of air through the system. In some embodiments, the air flow sensor is a solid state sensor and is shielded from the UV light source. The air flow sensor may also communicate with the microprocessor such that the microprocessor can control the fan speed based on a signal transmitted by the air flow sensor.

In some embodiments, the system can include a UV sensor located within the germicidal radiation chamber and configured to measure the amount of UV radiation. The UV sensor can be located in the air flow path. In addition, the UV sensor can communicate with the microprocessor such that the microprocessor can control the fan speed based on a signal transmitted by the UV sensor.

To prevent airflow through the system, the system may include a cover that has a closed and an open position. In the closed position the cover closes the system inlet when the system is not in use. The cover can be made from an insulating material. The cover can be connected to an interlock switch that senses the position of the cover and prevents system operation if the cover is in the closed position. The interlock switch can be connected to the microprocessor.

DETAILED DESCRIPTION OF SPECIFIC EMBODIMENTS

Figure 1:
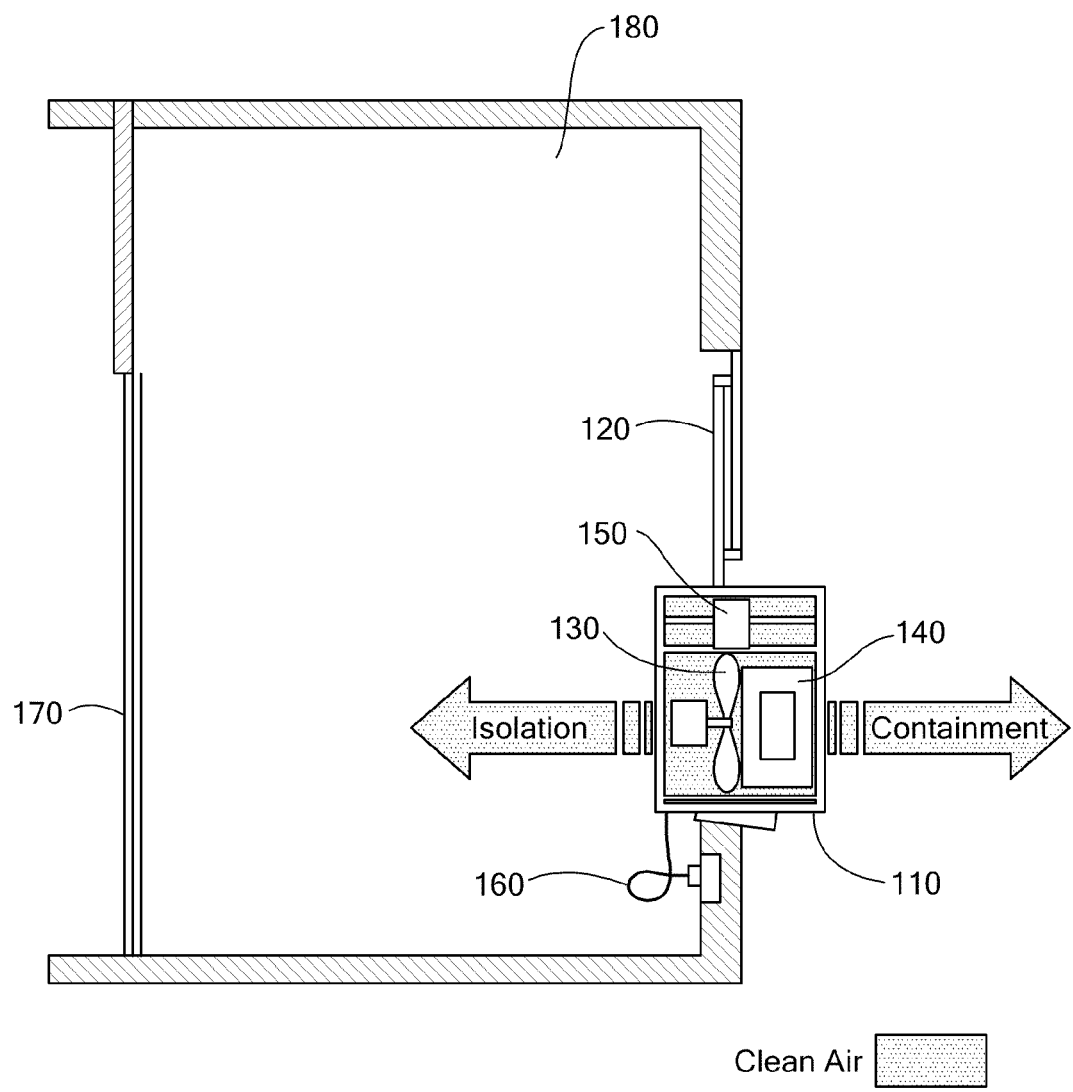
FIG. 1 shows an air-pressure-control system in accordance with an embodiment of the present invention.

FIG. 1 shows an air-pressure-isolation system 110 in accordance with the present invention. The system 110 may be a through window, "plug and play" type system. As such, the system 110 can transform a closed space 180 into either an isolation or containment room by placing the system 110 into a window 120 and plugging a power cord 160 into a standard wall socket. The inward facing side of the system 110 may have a stylish design so that it does not negatively impact the aesthetics of the closed space 180. The outward facing side of the system 110 may have a design that is suitable for exposure to the environment.

In an isolation configuration, a variable speed fan 130 forces clean air into the closed space 180, resulting in a positive pressure within the closed space 180. In order to produce a constant positive pressure consistent with surgical sites and clean rooms, the system 110 may control the air flow into the room, by varying the speed of the fan, to match the air flow out of the room through gaps around windows and doors. In the containment configuration, a variable-speed fan 130 forces air out of closed space 180, resulting in a negative room air pressure. In either orientation, a germicidal radiation chamber 140, located within a closed airflow path, cleans the air as it passes through system 110. If the system 110 is not installed in a window, the user can add an extension to the air path out of the germicidal radiation chamber 140 to reach the outside environment.

In some embodiments, the system 110 may contain multiple variable-speed fans. If more than one variable-speed fan is present, the fans may operate such that they force air in multiple directions.

Figure 2:
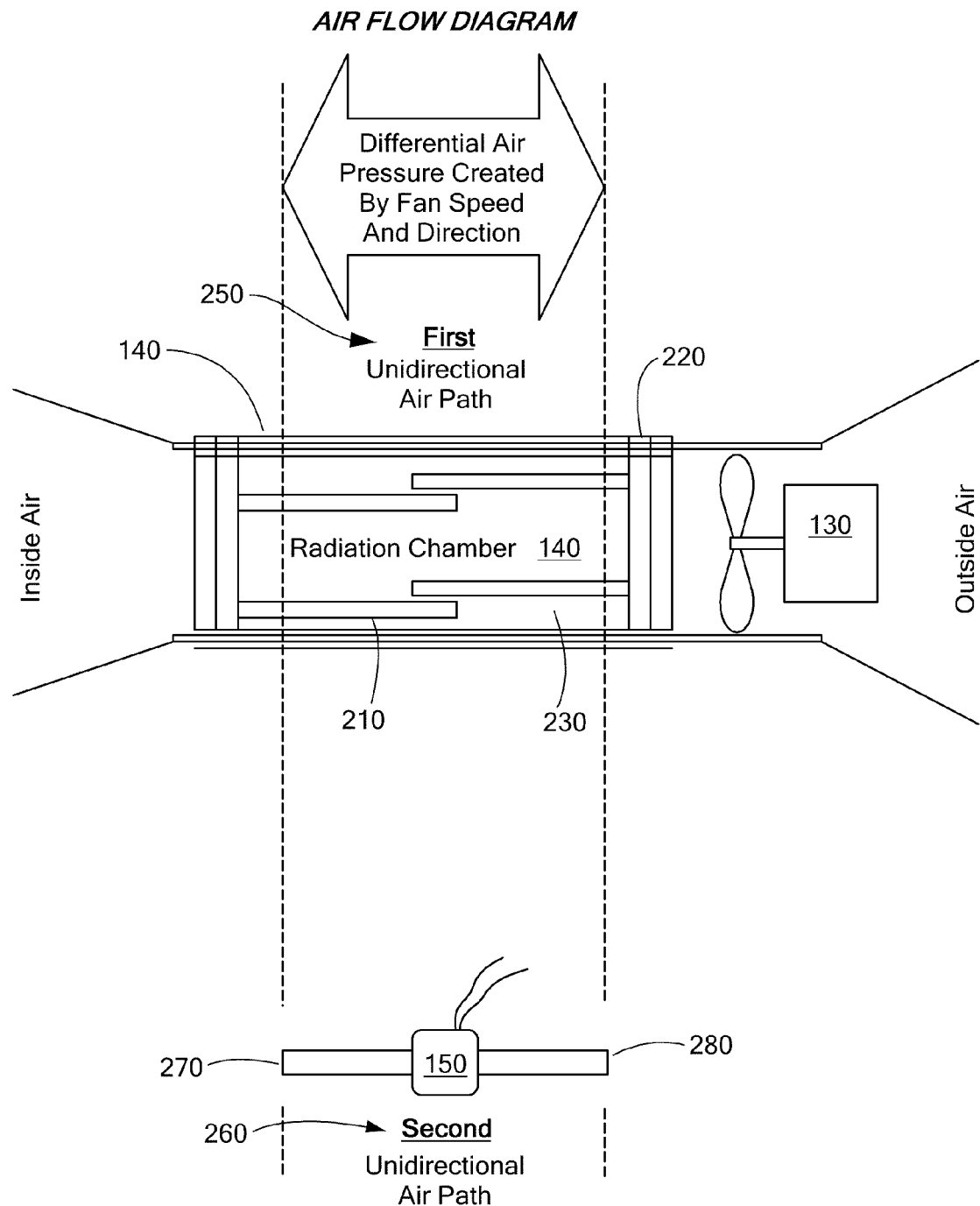
FIG. 2 shows an airflow diagram of the system shown in FIG. 1.

As show in FIG. 2, the germicidal radiation chamber 140 may contain ultraviolet lamps 210. The ultraviolet lamps 210 may radiate at a wavelength of approximately 253.7 nanometers. UV radiation at 253.7 nanometers has been proven to inflict the greatest amount of damage on living and dormant micro-organisms. For example, at 253.7 nanometer wavelength, UV testing on influenza indicates a 90% kill ratio with severe damage (sufficient to neutralize) inflicted on the remaining 10%. The targets of the germicidal radiation chamber 140 include, but are not limited to: viruses, bacteria, fungus, mold, and spores. Although a 253.7 nanometer wavelength is used as an example, the UV wavelength can be adjusted to maximize the damage to any one species of micro-organisms.

The radiation chamber 140 may also provide access to the UV lamps 210 so that a user may replace the UV lamps 210 when needed. The user can install the UV lamps 210 from outside of the germicidal radiation chamber 140 so that they need not disassemble the chamber 140. Access to the UV lamps 210 may include a kill switch that shuts off the system 110 to prevent a user from accessing the UV lamps 210 during operation. Alternatively, the germicidal radiation chamber 140 may be a cartridge design that a user can completely remove and replace at a remote location. The UV lamps 210 may include multiple lamps with varying wavelengths to target different types of airborne particulates or micro-organisms.

As mentioned above, the germicidal radiation chamber 140 can be removable. In embodiments containing a removable radiation chamber 140, the system may also include an interlock switch that is electrically connected to the radiation chamber 140. The interlock switch can verify that the radiation chamber 140 is installed correctly and, in the event of incorrect installation, cut off the main power to the system 110.

Destruction and neutralization of micro-organisms using UV light depends on the amount of UV light that the micro-organisms are exposed to and the exposure time. To increase the amount of exposure, the inside surface of the germicidal radiation chamber 140 may contain a reflective coating 230. The reflective coating 230 reflects the UV light within the chamber, exposing the micro-organisms to greater amounts of UV light and, thus, increasing the micro-organism kill and neutralization ratios. The exposure time may be increased by slowing down the air flow within the germicidal radiation chamber 140. A laminar air flow through chamber 140 can assure that the resident time and exposure is uniform and equal throughout chamber 140. To further increase the exposure and residence time, the chamber 140 should be as large as possible within the constraints of overall size of the system 110. Dead spots in the airflow should be minimized.

UV light is hazardous and should be contained within the germicidal radiation chamber 140 and system 110. To prevent UV light from escaping, the germicidal radiation chamber 140 may include baffles 220 at one or both ends. The airflow path of the system 110 may be blackened to prevent UV reflection through the system inlet or outlet.

A differential-air-pressure transducer 150 can measure the air pressure at the inlet and outlet of the system 110. The differential-air-pressure transducer 150 may sample and measure the air pressure of the inside air through a closed space air port 270 and can measure the outside air pressure through an outside air port 280. The system 110 may contain pressure-tight connections between the differential pressure transducer 150 and air ports 270, 280. The outside air port 280 may contain provisions to prevent blockage from freezing weather and other variables such as insects. If the system 110 is not installed in a window, the outside air port 280 may include an extension to reach the outside environment. In some embodiments, the differential-air-pressure sensor 150 can be a hot-wire or solid state anemometer. In other embodiments, a pressure transducer 150 may be located in a second airflow path 260. The second airflow path 260 may be separate and distinct from the first airflow path 250, which contains the germicidal radiation chamber 140.

Figure 3:
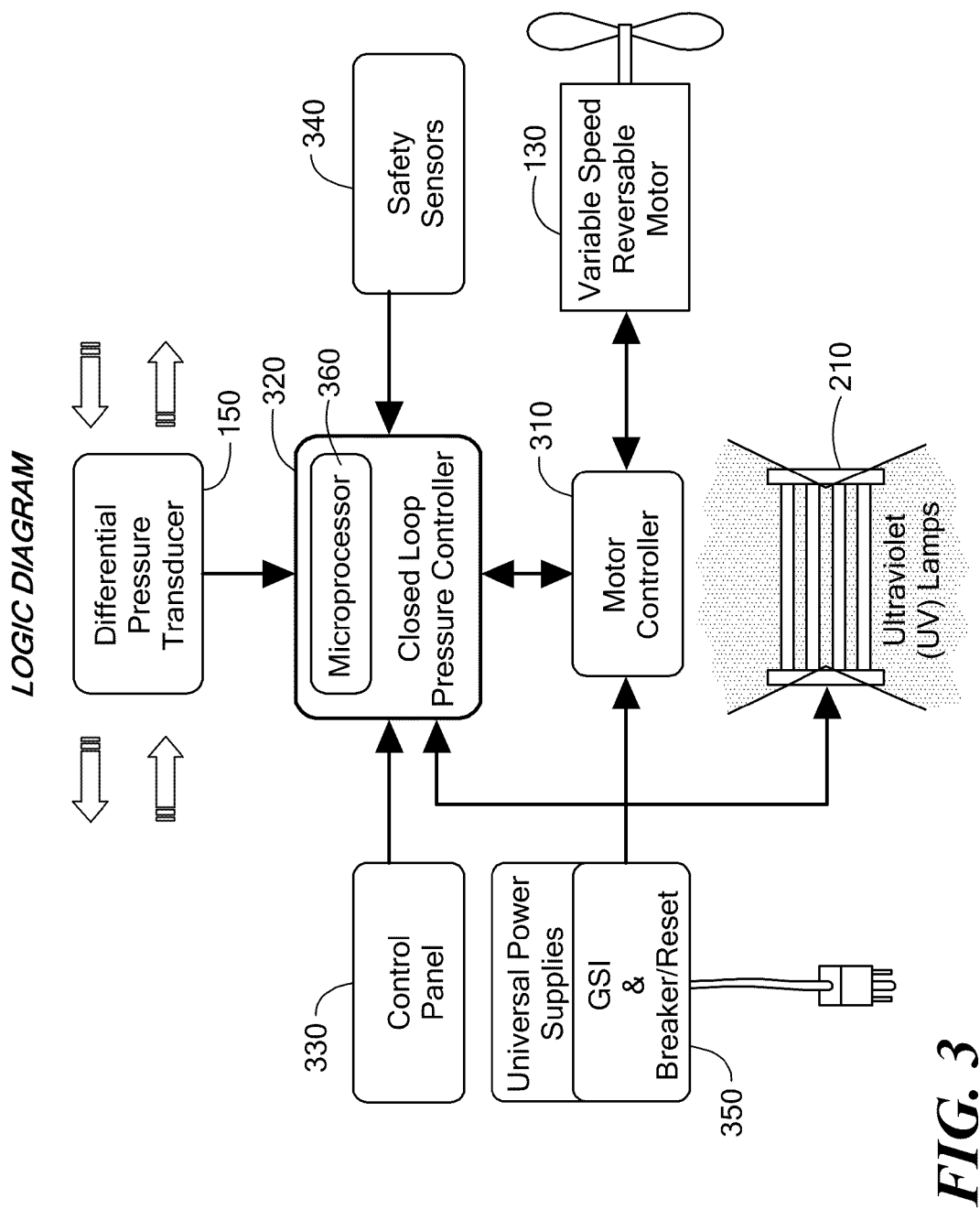
FIG. 3 shows a logic diagram of the system shown in FIG. 1.

As shown in FIG. 3, the system 110 may include a closed-loop controller 320. The closed-loop controller 320 may be connected to the differential-air-pressure transducer 150, and a motor controller 310. The closed-loop controller 320 may monitor the pressure differential between the system inlet and the system outlet and, based on the pressure differential, adjust the speed of the fan 130 via the motor controller 3 10. By controlling the speed of the fan 130 via the motor controller 310, the closed-loop controller 320 is able to control the pressure within the closed space 180. The motor controller 310 may work on all voltages and cycles, and have a selectable voltage switch. In embodiments containing multiple fans, the motor controller 310 may have a different controller power situation for each unit.

During startup, the closed-loop controller 320 may be configured to expect a worst case scenario and bring the fan 130 to full speed. In response to a power interruption to the system 110, the closed-loop controller 320 may provide an orderly shut down and start up process.

The closed-loop controller 320 may include a microprocessor 360. The microprocessor 360 may compare the differential-air-pressure transducer 150 output to a setpoint inputted by the user via a control panel 330 (discussed below). The microprocessor 360 may then adjust the speed of the fan 130 to maintain the pressure within the closed space 180 at the setpoint value. When the system 110 is operating out of set point conditions, the closed-loop controller 320 may trigger an alarm.

The closed-loop controller 320 may also include a second control band capable of recognizing when a door 170 (FIG. 1) is opened. The closed-loop controller 320 may then respond to such a condition by taking the fan 130 to full speed and then closing on a setpoint. The closed-loop controller 320 may also set a dead band to prevent the fan 130 from hunting.

In other embodiments, the closed-loop controller 320 may verify the presence of UV light and control the intensity of the UV radiation based on the air flow through the system 110. The closed-loop controller 320 may control the intensity of the UV radiation by turning on all UV lamps 210 for maximum radiation, or by turning on one UV lamp at a time to perform a step function of radiation levels. The closed-loop controller 320 may also recognize if a UV lamp fails and switch the power to a functioning lamp.

In some embodiments of the present invention, the closed-loop controller may contain a software port (not shown). The software port allows a user to download new software revisions and to test individual functions of the system 110.

In further embodiments, the system 110 may contain a control panel 330. A user may input setpoints values into the control panel 330. The control panel 330 may also contain a switch (not shown) to allow the user to chose between either positive or negative room pressure. The switch can be either a mechanical switch, a key pad, or a key pad multiple digital code. In embodiments containing multiple fans, the control panel 330 may allow the user to select one of the fans to move in a different direction. Other functions of the control panel 330 include, but are not limited to, diagnosing one or all functions of the control system, and displaying when routine services, such as UV lamp 210 replacements, are needed. The control panel 330 may be available in multiple languages.

In accordance with other embodiments of the present invention, the system 110 may also contain safety sensors 340. The safety sensors 340 may include an audible or visible alarm. The safety sensor 340 and the associated alarm may be in communication with the microprocessor 360 and the closed-loop controller 320. After receiving a signal from the closed-loop controller 320, the safety sensor 340 may trigger the alarm if the system 110 is not operating at the setpoint value or when system components are not functioning.

A universal power supply 350 supplies power to the system 110. The power supply 350 contains a GSI and a breaker reset and may be plugged into a standard wall socket.

In another embodiment of the present invention, the system 110 is a filter-less system. In the filter-less embodiment, the UV light kills or neutralizes the micro-organisms as they pass through the germicidal radiation chamber 140.

Figure 4:
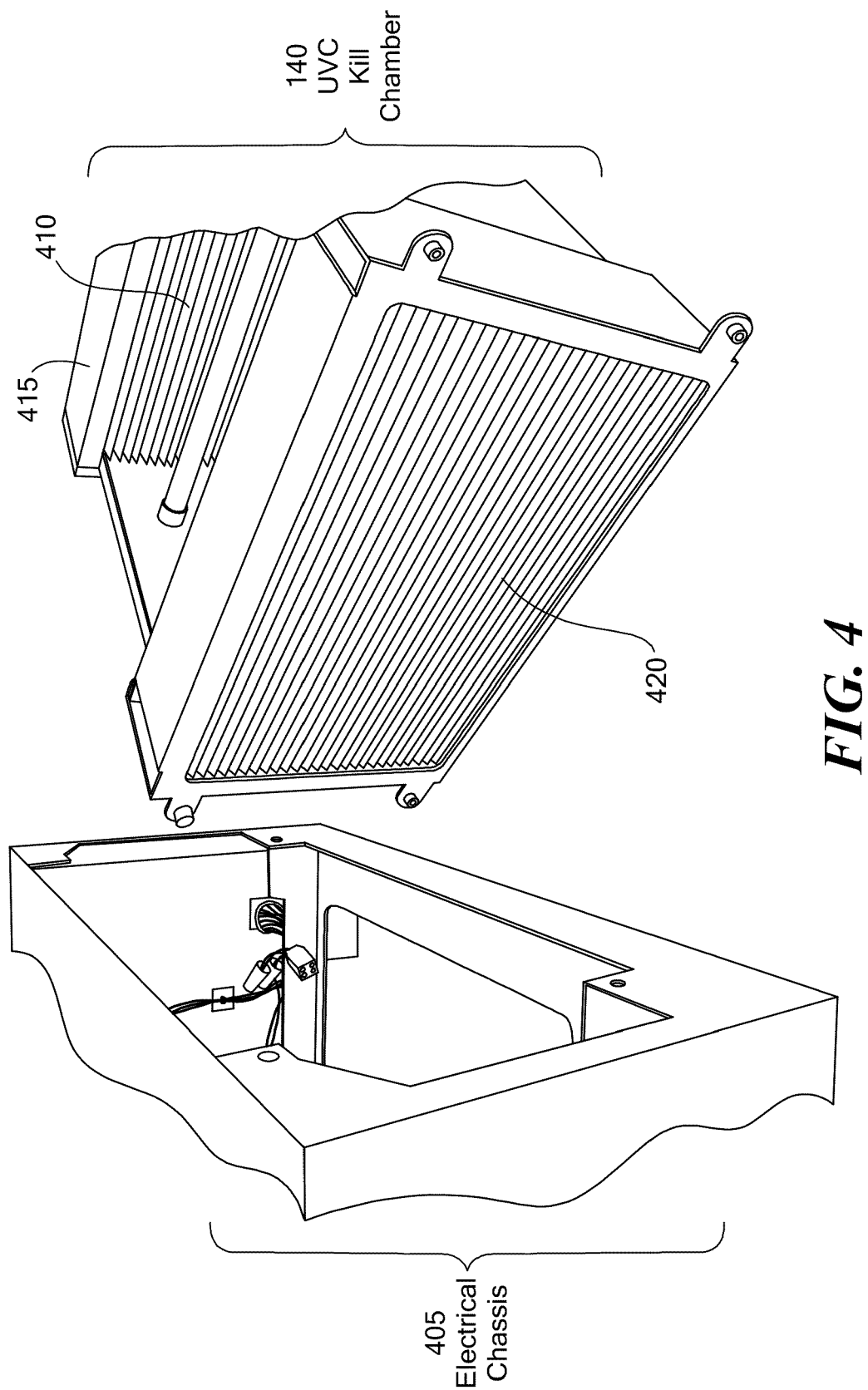
FIG. 4 shows an exemplary germicidal radiation chamber and electrical chassis in accordance with embodiments of the present invention.

As shown in FIG. 4, the germicidal radiation chamber 140 can be contained within an electrical chassis 405. In such embodiments, a user can essentially slide the germicidal radiation chamber 140 into the electric chassis 405 to create the complete system 110. As discussed in greater detail below, the electrical chassis 405 houses many of the electrical and mechanical components of the system 110.

Figure 5:
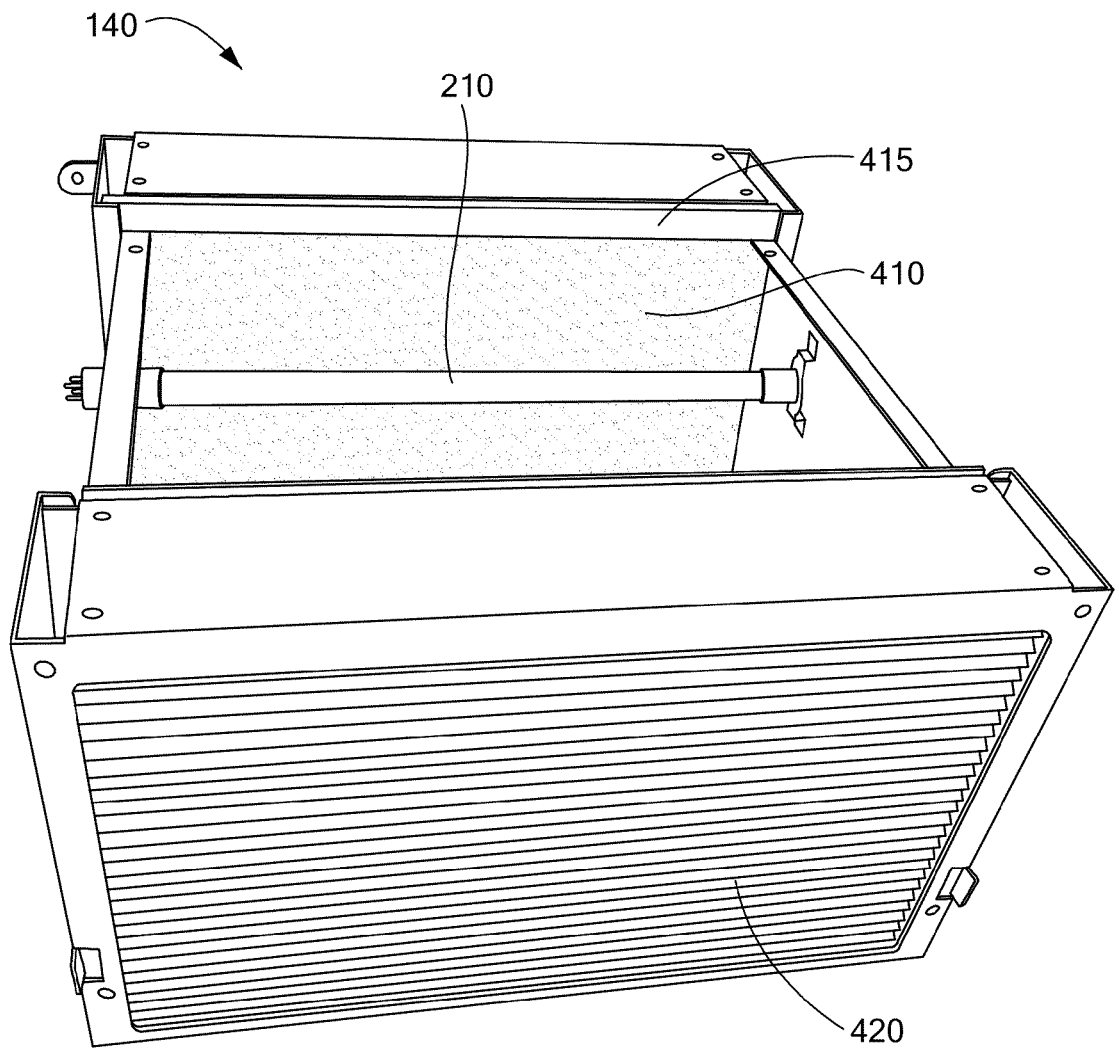
FIG. 5 shows the exemplary germicidal radiation chamber of FIG. 4 in accordance with embodiments of the present invention.

In still other embodiments and as shown in FIGS. 4 and 5, the system 110 may include a HEPA filter 410 located at one or both ends of the germicidal radiation chamber 140. In some embodiments, the filter 410 may be at the opposite end of the germicidal radiation chamber 140 from the fans 910 (see FIGS. 7 and 10). To ease filter installation and replacement, the germicidal radiation chamber 140 may include slots that allow access to the filter 410. The addition of the filter 410 and two more sensors (an air flow sensor in the UVC chamber and a UVC level sensor in the UVC chamber, discussed in greater detail below) essentially makes the system 110 a portable air cleaner and air sterilizer as well as a room isolation controller and a room containment controller.

In preferred embodiments, the filter 410 should be a translucent fiber glass HEPA filter. The translucent filter allows the UV radiation to pass through the filter, allowing the UVC radiation to kill the viruses as they move through the germicidal radiation chamber 140 and pass through the filter 410. In some embodiments, the filter may be pleated to increase the effective surface area of the filter. The pleated filters can be oriented such that the pleats are vertical, and the axis of the UV lamp 210 is transverse to the filter pleat axis. In preferred embodiments, the UV lamps 210 are co-planar.

The HEPA filter 410 will trap larger contamination, exposing the larger contamination to continuous irradiation by the high intensity UVC lamps 210. By doing so, the filter 410 allows for destruction of the larger particulates (which require greater amounts or irradiation to be killed), while maintaining a manageable system size and the flowrates needed for room isolation and containment. The UVC radiation will dissociate most organic particulates from the HEPA filter 410, creating a self-cleaning filter.

The filter 410 and filter frame 415 (FIG. 7) should be constructed from materials that are resistant to UVC radiation. For example, the filter 410 may be translucent fiber glass, and the filter frame 415 may be metal.

The entrance to the germicidal radiation chamber 140 can also include a UVC light baffle and flow straightener 420. As discussed above, the UVC light baffles prevent UV light from exiting the germicidal radiation chamber 140. As the name suggests, the flow straighteners straighten the air flow through the system and may be used to reduce turbulence within the germicidal radiation chamber 140.

Figure 6:
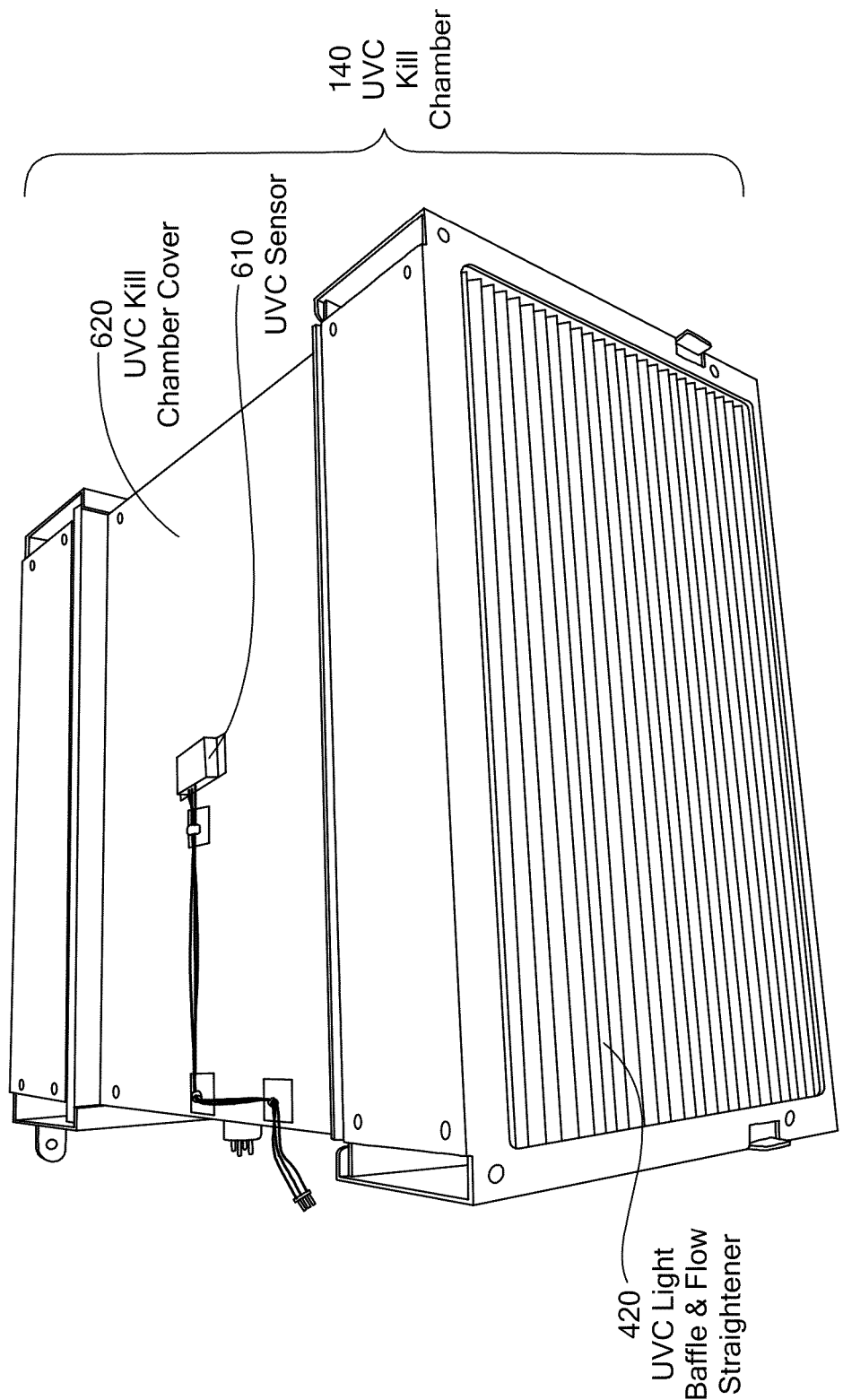
FIG. 6 shows the germicidal radiation chamber of FIG. 4 with a chamber cover and UVC sensor in accordance with embodiments of the present invention.

As shown in FIG. 6, the germicidal radiation chamber 140 can have a cover 620 that encases the germicidal radiation chamber 140. In addition, some embodiments of the present invention may also have a UV level sensor 610 located within the germicidal radiation chamber 140. The UV level sensor 610 can either be in or at the edge of the air flow. The UV level sensor 610 can transmit a signal to the microprocessor, which may control the fan speed or indicator lights based on the UV level sensor signal.

Figure 7:
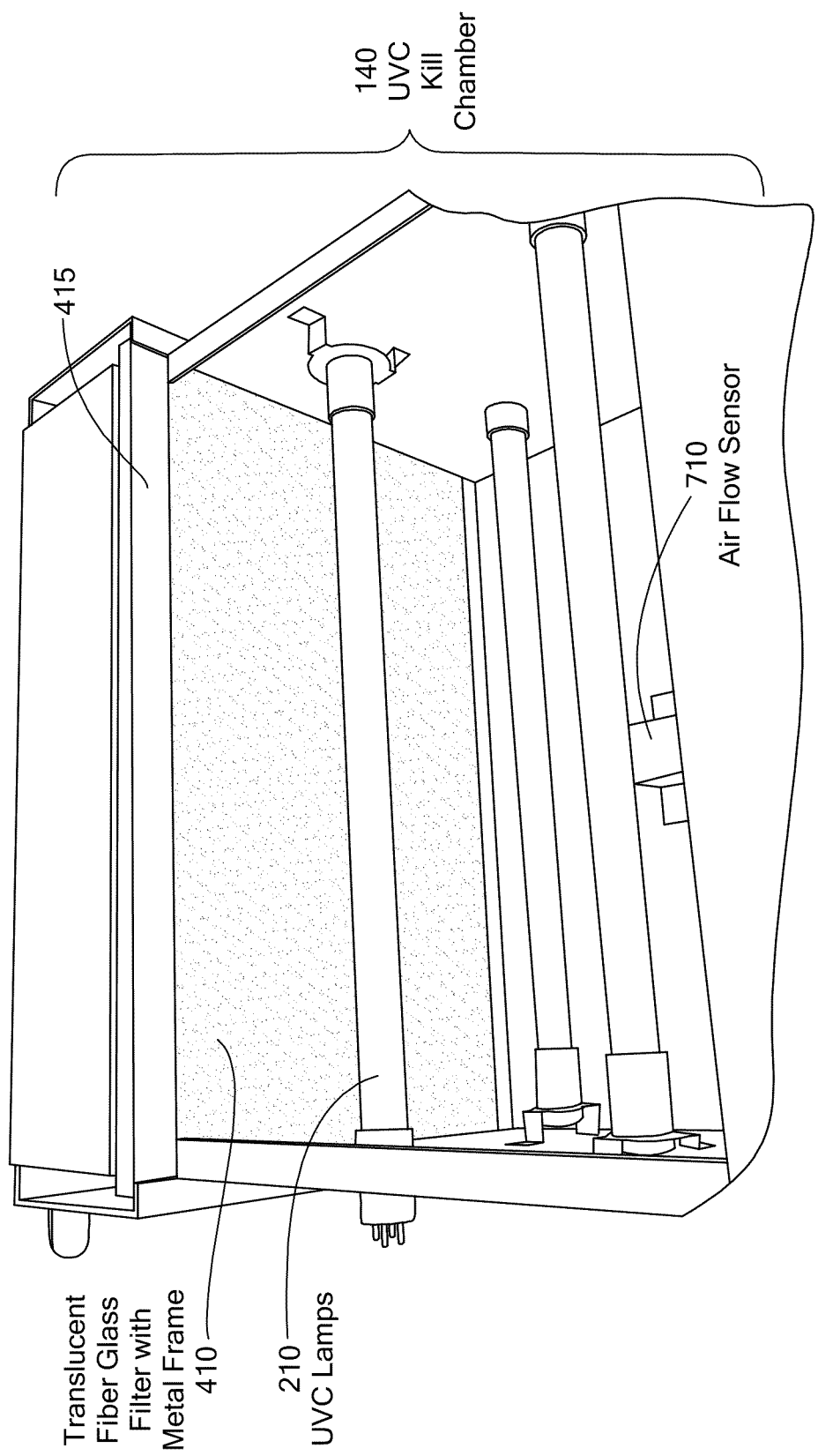
FIG. 7 shows the inside of the germicidal radiation chamber of FIG. 4 in accordance with embodiments of the present invention.
Figure 8:
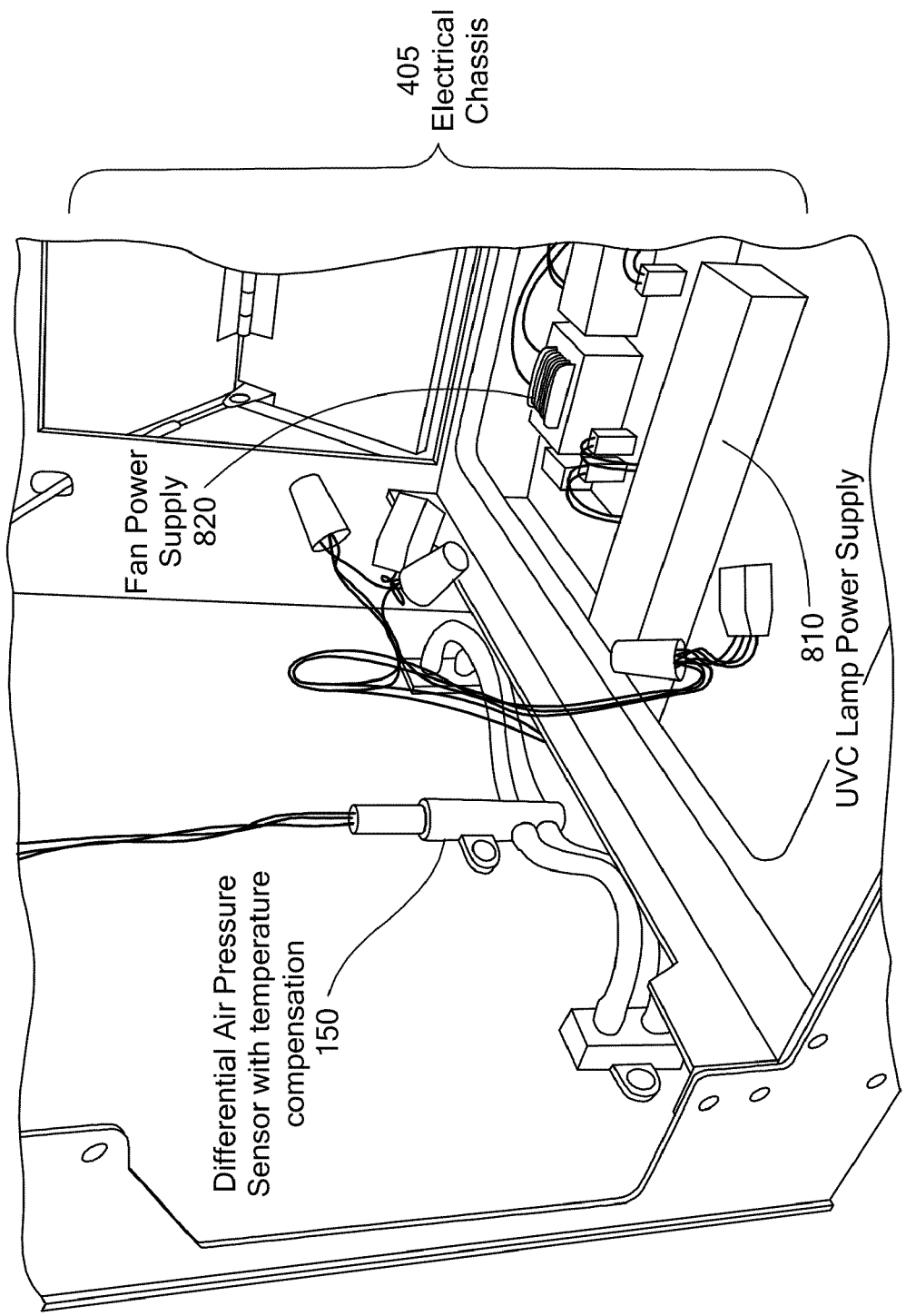
FIG. 8 shows the inside of the electrical chassis of FIG. 4 in accordance with embodiments of the present invention.

As shown in FIG. 7, the system 110 may also include an air flow sensor 710 located within the germicidal radiation chamber 140 (e.g., mounted to the inside wall of the chamber) and connected to the microprocessor. In preferred embodiments, the air flow sensor should 710 be a solid state sensor and co-linear with the air flow. In addition, the air sensor 710 should be shielded from the UV radiation to prevent damage to the air flow sensor 710. The air flow sensor 710 can send a signal to the microprocessor indicative of the air flow through the system. The microprocessor may then use this signal to modify the fan speed or control an indicator light (e.g., an alarm). In some embodiments, the air flow sensors 710 can be temperature compensated.

In addition to the above described components, the electrical chassis 405 can also house the UVC power supply 810 and the fan power supply 820. The electrical chassis 405 can also house the differential air pressure sensor 150. In a similar manner as the flow sensors 710, the differential air pressure sensor 150 can be temperature compensated.

Figure 9:
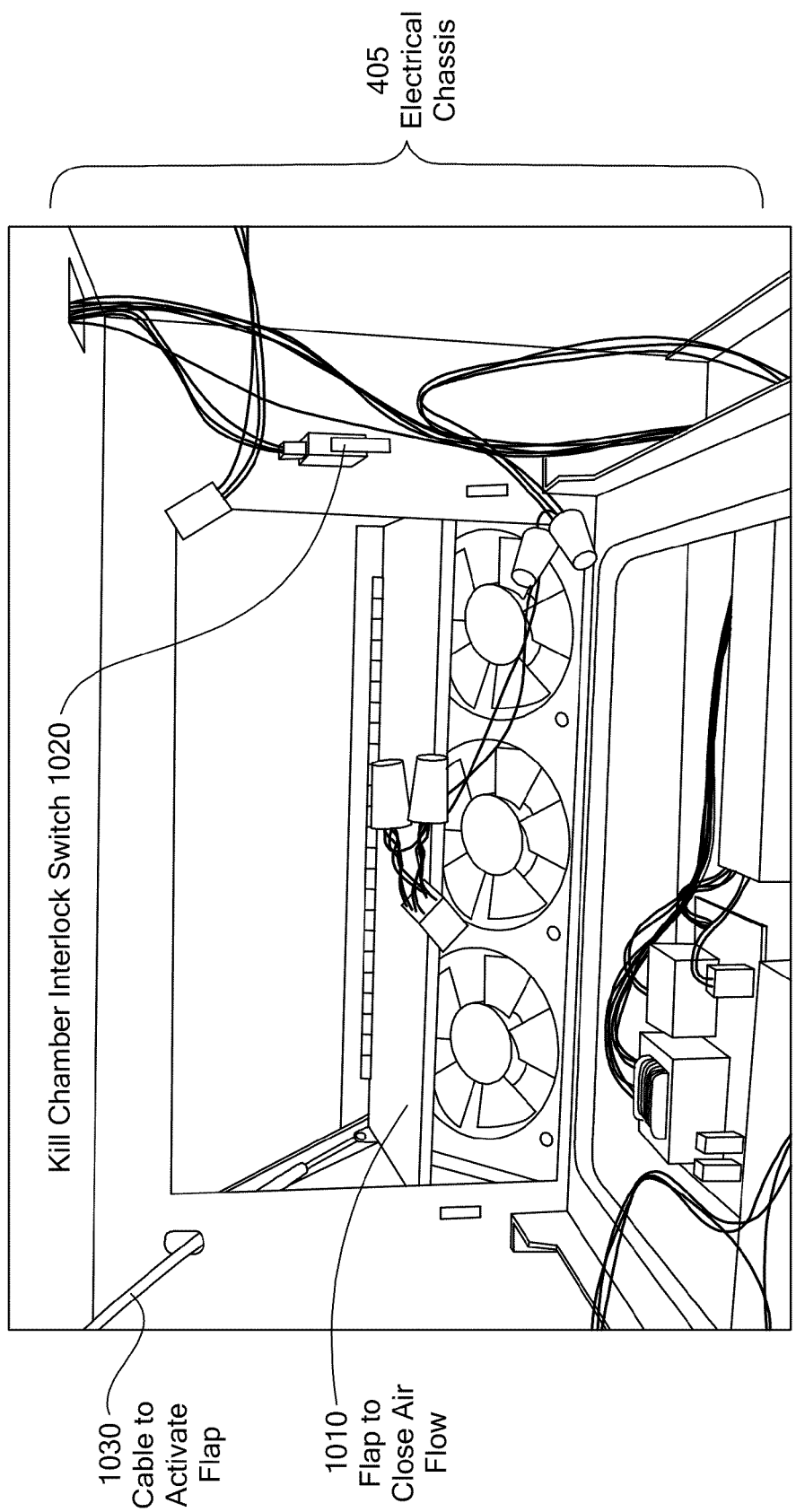
FIG. 9 shows another view of the internals of the exemplary electrical chassis shown in FIG. 4 in accordance with embodiments of the present invention.

As shown in FIG. 9, to improve system storage and prevent debris, dirt, and other objects from collecting within the system 110, the system 110 may also have a cover 1010 that closes off the air flow when the system is not in use. The cover 1010 may be, for example, a slide or a flap made from an insulating material. In some embodiments, the system may include a cover interlock switch 1020 electrically connected to the cover 1010 to sense the position of the cover 1010 (e.g., whether the cover is open or closed). The cover interlock switch 1020 may also be electrically connected to the microprocessor such that it prevents system operation when the cover 1010 is closed.

In some embodiments, a cable 1030 can be used to activate (e.g., open and close) the cover 1010. The position of the cable 1030 can act as the on-off switch for the system. For example, when the cable position corresponds to an open cover, the system is on. Conversely, when the cable position corresponds to a closed cover, the system is off. Like the cover 1010 itself, the cable 1030 can also be electrically connected to a cable interlock switch 1050 (FIG. 10) to sense the position of the cable 1030. A user can adjust the position of the cable 1030 (e.g., open and close) using a knob 1040 located on the system control panel 330 (FIG. 11).

Figure 10:
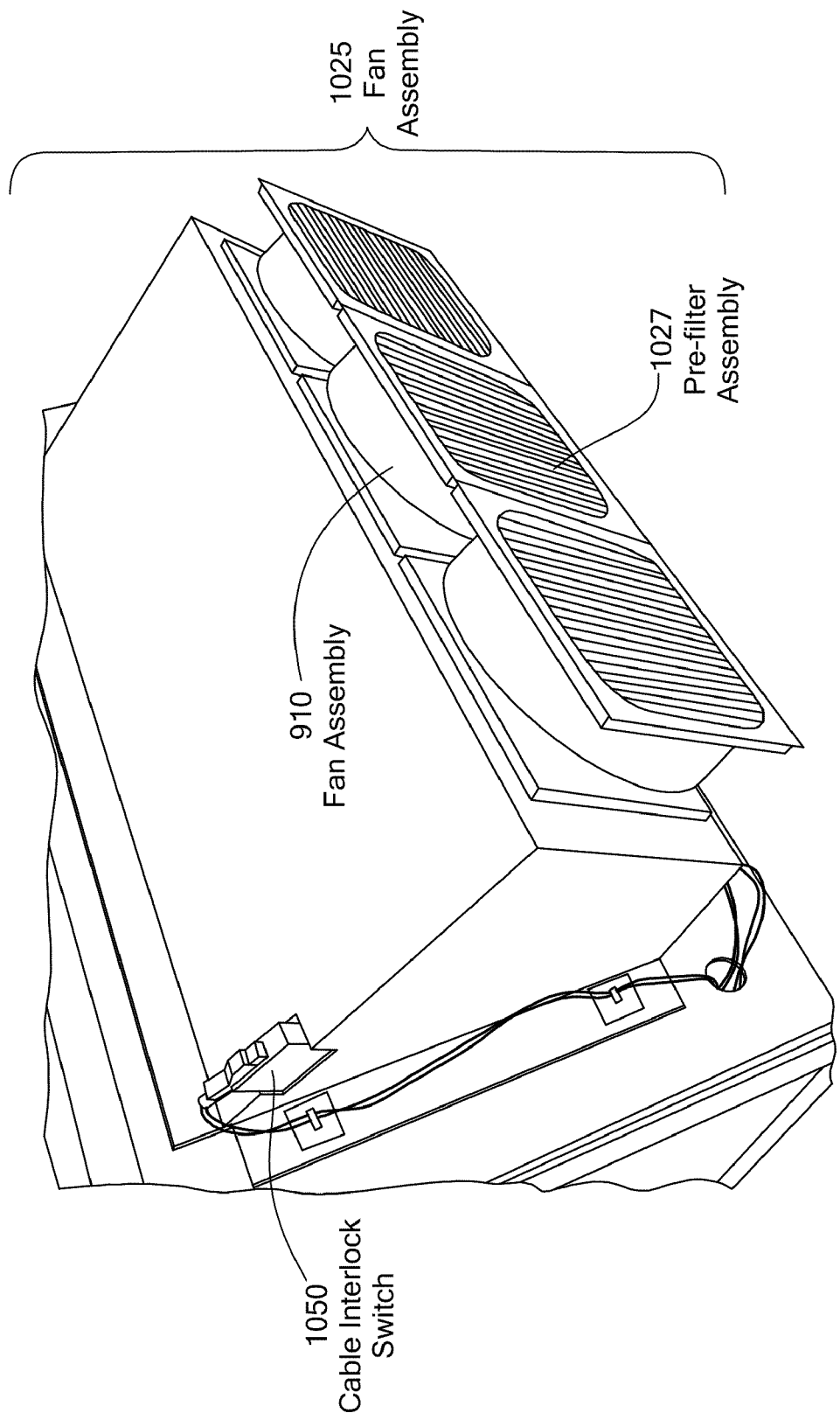
FIG. 10 shows a fan assembly with pre-filter in accordance with an embodiment of the air-pressure control system.
Figure 11:
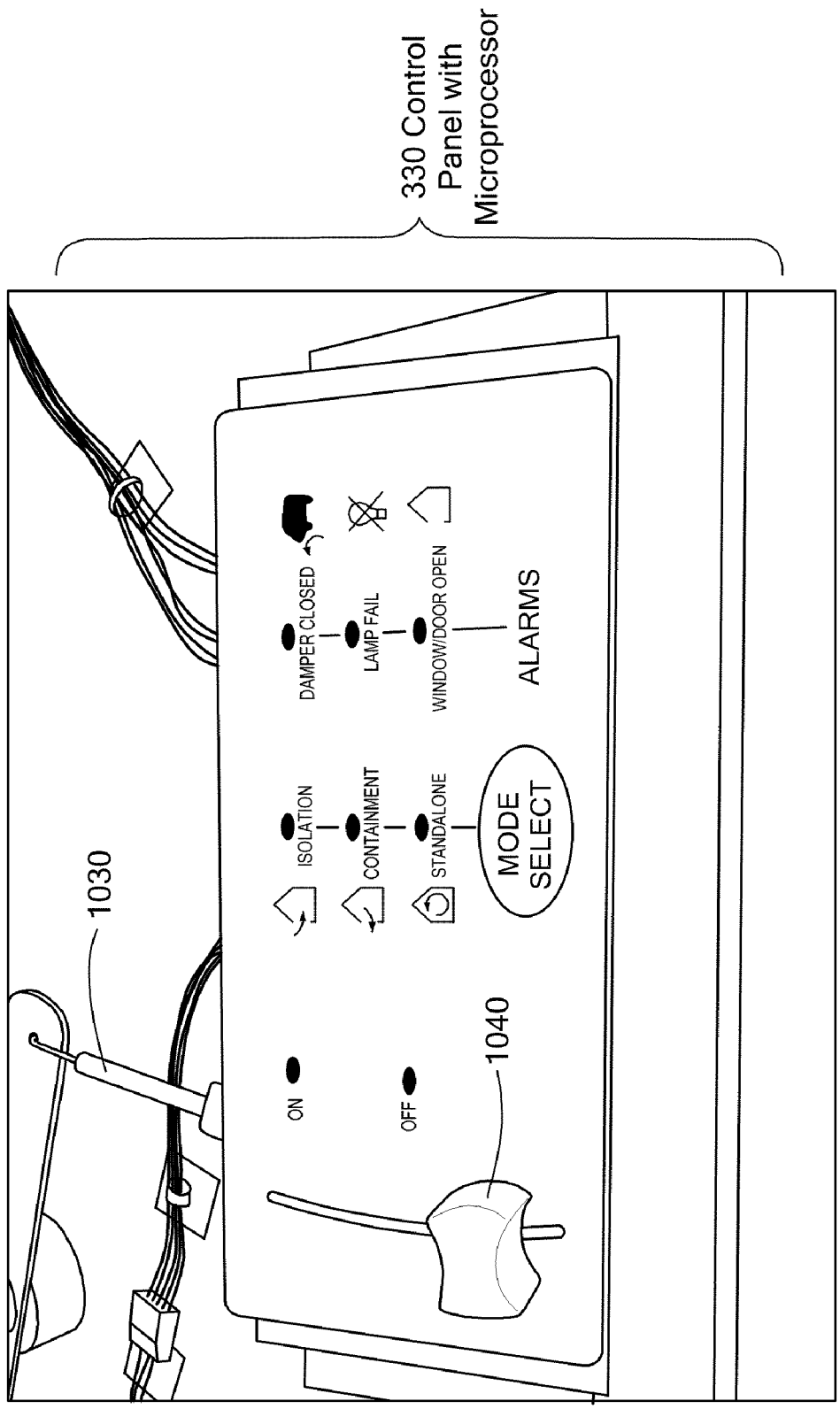
FIG. 11 shows an exemplary control panel in accordance with embodiments of the present invention.

As shown in FIG. 10, the system can have a fan assembly 1025 attached to the electrical chassis 405. The fan assembly can have any number of fans (FIG. 10 shows 3 fans) that create the air flow through the system. As mentioned above, the fan speed can be controlled based on a number of criteria including, but not limited to, pressure differential, set points, and amount of UV light. The fan assembly 1025 can have a pre-filter assembly 1027 that covers each of the fans. The pre-filter assembly 1027 prevents larger objects, debris, or small animals from entering the system 110.

In some embodiments, the portion of the system 110 exposed to the outside elements may have insulation 1205

Figure 12:
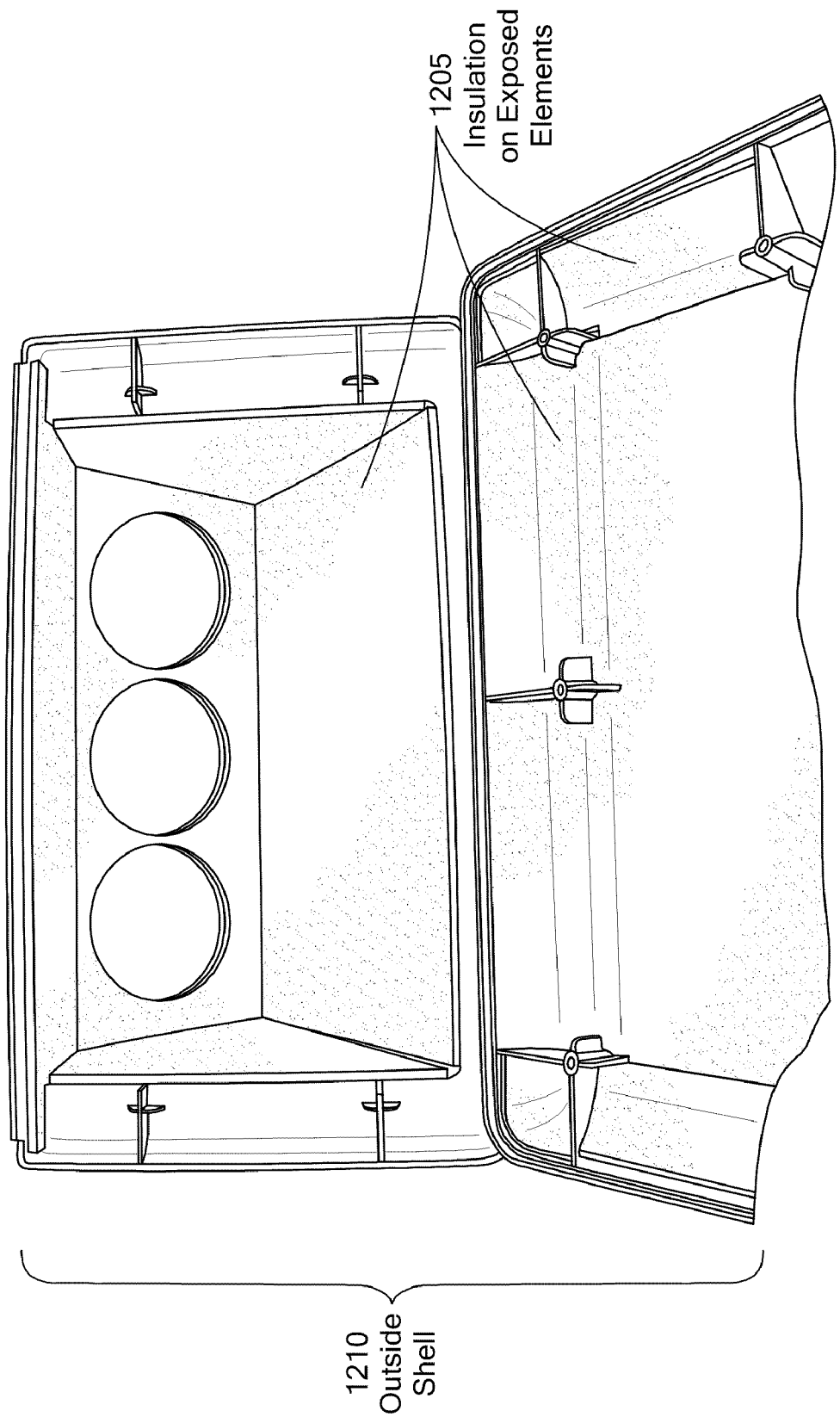
FIG. 12 shows an exemplary outside shell with insulation on exposed elements in accordance with embodiments of the present invention.

(FIG. 12). In addition, the outside shell 1210 may receive an expandable frame (not shown) that provides for a better fit in through-window installations. The expandable frame can expand to the size of the window in which the system is installed. The expandable frame may include a soft gasket for sealing against the window sill, window frame, and the system shell.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. An air-pressure-control system, the system comprising:
   a system inlet;
   a system outlet;
   a variable-speed fan configured to operate at a speed;
   a motor controller in communication with the fan and configured to control the speed of the fan;
   a differential-air-pressure transducer configured to monitor an air pressure differential between the system inlet and the system outlet; and
   a closed-loop controller in communication with the motor controller and the differential-air-pressure transducer, wherein the closed-loop controller is configured to vary the speed of the fan based on the pressure differential between the inlet and outlet of the system, thereby controlling a pressure within a space; and
   an interface in communication with the closed-loop controller and configured to receive a setpoint value, the closed-loop controller bringing the fan to full speed upon a change in condition within the space, the closed-loop controller then reducing the speed of the fan to obtain the setpoint value.

2. An air-pressure-control system according to claim 1, wherein the interface is a control panel.

3. An air-pressure-control system according to claim 2, wherein the control panel includes a switch configured to select between positive and negative room air pressures.

4. An air-pressure-control system according to claim 2, wherein the control panel includes a keypad.

5. An air-pressure-control system according to claim 1, wherein the closed-loop controller includes:
   a microprocessor configured to compare an output from the differential-air-pressure transducer and the setpoint value and adjust the speed or direction of the fan based on the difference between the differential-air-pressure transducer output and the setpoint value.

6. An air-pressure-control system according to claim 5, further comprising a safety sensor in communication with the microprocessor and configured to alarm when the air-pressure-control system is not operating at the setpoint values.

7. An air-pressure-control system according to claim 5, further comprising:
   a germicidal radiation chamber located within an airflow path in the air-pressure-control system, wherein the germicidal radiation chamber includes at least one UV light source.

8. An air-pressure-control system according to claim 7, wherein the germicidal radiation chamber further includes a reflective interior surface configured to reflect UV light produced by the UV light source.

9. An air-pressure-control system according to claim 7, wherein the airflow path is blackened to prevent UV reflection through the system inlet and system outlet.

10. An air-pressure-control system according to claim 7, wherein the germicidal radiation chamber is a removable cartridge.

11. An air-pressure-control system according to claim 7, wherein the microprocessor controls the operation of the at least one UV light source.

12. An air-pressure-control system according to claim 7, further comprising at least one baffle located at an least one end of the germicidal radiation chamber, wherein the at least one baffle is configured to prevent UV light from exiting the germicidal radiation chamber.

13. An air-pressure-control system according to claim 12, wherein the at least one baffle straightens the air flow through the system.

14. An air-pressure-control system according to claim 12, wherein the at least one baffle is blackened to prevent UV reflection through the system inlet and system outlet.

15. An air-pressure-control system according to claim 7, wherein the UV light has a wavelength of about 253.7 nanometers.

16. An air pressure control system according to claim 7, the system further including an air flow sensor located within the germicidal radiation chamber.

17. An air pressure control system according to claim 16, wherein the air flow sensor is mounted on an inside wall of the germicidal radiation chamber.

18. An air pressure control system according to claim 16, wherein the air flow sensor is oriented such that it is co-linear with a flow of air through the system.

19. An air pressure control system according to claim 16, wherein the air flow sensor is a solid state sensor.

20. An air pressure control system according to claim 16, wherein the air flow sensor is shielded from the at least one UV light source.

21. An air pressure control system according to claim 16, wherein the air flow sensor is in communication with the microprocessor such that the microprocessor can control the fan speed based on a signal transmitted by the air flow sensor.

22. An air pressure control system according to claim 7, the system further comprising a UV sensor located within the germicidal radiation chamber and configured to measure an amount of UV radiation.

23. An air pressure control system according to claim 22, wherein the UV sensor is located in the air flow path.

24. An air pressure control system according to claim 22, wherein the UV sensor is in communication with the microprocessor such that the microprocessor can control the fan speed based on a signal transmitted by the UV sensor.

25. An air-pressure-control system according to claim 7, wherein the differential-air-pressure transducer is an anemometer.

26. An air-pressure-control system according to claim 7, wherein the air-pressure-control system is configured for through-window installation.

27. An air-pressure-control system according to claim 7, further comprising a first filter located within the airflow.

28. An air-pressure-control system according to claim 27, wherein the first filter is a HEPA filter.

29. An air-pressure-control system according to claim 28, wherein the germicidal radiation chamber has at least one slot providing access to the filter.

30. An air-pressure-control system according to claim 29, wherein the first filter is located at a first end of the germicidal radiation chamber.

31. An air-pressure control system according to claim 30, wherein the system includes a second filter located at a second end of the germicidal radiation chamber.

32. An air-pressure control system according to claim 27, wherein the first filter is a translucent glass fiber filter.

33. An air-pressure control system according to claim 27, wherein the first filter has a metal frame.

34. An air-pressure control system according to claim 27, wherein the first filter is pleated.

35. An air-pressure control system according to claim 34, wherein the first filter is oriented such that the pleats are oriented vertically.

36. An air-pressure control system according to claim 35, wherein the at least one UV light source is oriented such that it is transverse to the pleats of the first filter.

37. An air pressure control system according to claim 1, the system further comprising a cover having a closed and open position configured to close the system inlet when the system is not in use, thereby preventing airflow through the system.

38. An air pressure control system according to claim 37, wherein the cover is made from insulating material.

39. An air pressure control system according to claim 37, the system further comprising an interlock switch connected to the cover and configured to sense a position of the cover and prevent system operation if the cover is in the closed position.

40. An air pressure control system according to claim 39, the system further comprising:
a germicidal radiation chamber located within an airflow path in the air-pressure-control system, wherein the germicidal radiation chamber includes at least one UV light source, wherein the interlock switch is connected to a microprocessor.

41. An air pressure control system according to claim 1, wherein the closed-loop controller includes a software port for downloading new software to the system.

42. An air pressure control system, the system comprising:
a first air path including a first air path inlet and first air path outlet;
a second air path including a second air path inlet and second air path outlet;
a variable-speed fan located within the first unidirectional air path and configured to operate at a speed;
a motor controller in communication with the variable-speed fan and configured to control the speed of the variable-speed fan;
a differential-air-pressure transducer located within the second air path and configured to monitor an air pressure differential between the second air path inlet and the second air path outlet;
a closed-loop controller in communication with the motor controller and differential-air-pressure transducer, wherein the closed-loop controller is configured to maintain a pressure in a space by varying the speed of the fan based on the pressure differential between the air pressure at the second air path inlet and the air pressure at the second air path outlet; and
a germicidal radiation chamber located within the first airflow path in the air-pressure-control system, wherein the germicidal radiation chamber includes at least one UV light source, and wherein the first airflow path is blackened to prevent UV reflection through the system inlet and system outlet.

43. An air-pressure-control system according to claim 42, further comprising:
a control panel in communication with the closed-loop controller and configured to receive setpoint values and to change the speed or a direction of the fan based on the setpoint value.

44. An air pressure control system according to claim 43, wherein the control panel includes a switch configured to select between positive and negative closed space air pressures.

45. An air-pressure-control system according to claim 43, wherein the closed-loop controller includes:
a microprocessor configured to compare an output from the differential-air-pressure transducer and the setpoint value and adjust the speed or direction of the fan based on the difference between the differential-air-pressure transducer output and the setpoint value.

46. An air-pressure-control system according to claim 45, further comprising a safety sensor in communication with the microprocessor and configured to alarm when the air-pressure-control system is not operating at the setpoint values.

47. An air-pressure-control system according to claim 42, wherein the germicidal radiation chamber further includes a reflective interior surface configured to reflect UV light produced by the UV light source.

48. An air pressure control system according to claim 47, wherein air flow through the system is laminar, the reflective interior surface being parallel to the laminar flow.

49. An air pressure control system according to claim 42, further comprising baffles located at an least one end of the germicidal radiation chamber, wherein the baffles are configured to prevent UV from exiting the germicidal radiation chamber.

50. An air-pressure-control system according to claim 42, wherein the UV light has a wavelength of about 253.7 nanometers.

51. An air-pressure-control system according to claim 42, wherein the differential-air-pressure transducer is an anemometer.

52. An air-pressure-control system according to claim 42, wherein the air-pressure-control system is configured for through-window installation.

53. An air-pressure-control system according to claim 42, wherein the first air path and the second air path are reversible.

54. An air-pressure-control system according to claim 42 further comprising a first filter located within the first airflow path.

55. An air-pressure-control system according to claim 54, wherein the germicidal radiation chamber has
at least one slot providing access to the filter.

56. An air-pressure-control system according to claim 55, wherein the first filter is located at a first end of the germicidal radiation chamber.

57. An air pressure control system according to claim 56, wherein the system includes a second filter located at a second end of the germicidal radiation chamber.

58. An air pressure control system according to claim 55, wherein the first filter is translucent.

59. An air-pressure-control system according to claim 55, wherein the first filter has a metal frame.

60. An air-pressure-control system according to claim 55, wherein the first filter is pleated.

61. An air-pressure-control system according to claim 55, wherein the first filter is oriented such that the pleats are oriented vertically.

62. An air-pressure-control system according to claim 55, wherein the at least one UV light source is oriented such that it is transverse to the pleats of the first filter.

63. An air pressure control system according to claim 42, the system further comprising a cover having a closed and open position configured to close the system inlet when the system is not in use, thereby preventing airflow through the system.

64. An air-pressure-control system, the system comprising:
   a system inlet;
   a system outlet;
   a variable-speed fan configured to operate at a speed;
   a motor controller in communication with the fan and configured to control the speed of the fan;
   a differential-air-pressure transducer configured to monitor an air pressure differential between the system inlet and the system outlet; and
   a closed-loop controller in communication with the motor controller and the differential-air-pressure transducer, wherein the closed-loop controller is configured to vary the speed of the fan based on the pressure differential between the inlet and outlet of the system, thereby controlling a pressure within a space, the closed-loop controller including a microprocessor configured to compare an output from the differential-air-pressure transducer and the setpoint value and adjust the speed or direction of the fan based on the difference between the differential-air-pressure transducer output and a setpoint value; and
   a germicidal radiation chamber located within an airflow path in the air-pressure-control system, wherein the germicidal radiation chamber includes at least one UV light source, the microprocessor controlling the operation of the at least one UV light source.

65. An air-pressure-control system according to claim 64, wherein the closed-loop controller brings the fan to full speed upon a change in condition within the space, the closed-loop controller then reducing the speed the fan to obtain the setpoint value.

66. An air-pressure-control system according to claim 64, further comprising a control panel, the control panel including a switch configured to select either a positive or a negative room air pressures.

67. An air-pressure-control system according to claim 64, further comprising a safety sensor in communication with the microprocessor and configured to alarm when the air-pressure-control system is not operating at the setpoint value.

68. An air-pressure-control system according to claim 64, wherein the microprocessor controls the operation of the at least one UV light source.

69. An air-pressure-control system according to claim 64, further comprising at least one baffle located at an least one end of the germicidal radiation chamber, wherein the at least one baffle is configured to prevent UV light from exiting the germicidal radiation chamber.

70. An air-pressure-control system according to claim 69, wherein at least a portion of an edge of the at least one baffle is in contact with the germicidal radiation chamber.

71. An air pressure control system according to claim 64, the system further including an air flow sensor located within the germicidal radiation chamber.

72. An air pressure control system according to claim 71, wherein the air flow sensor is in communication with the microprocessor such that the microprocessor can control the fan speed based on a signal transmitted by the air flow sensor.

73. An air pressure control system according to claim 64, the system further comprising a UV sensor located within the germicidal radiation chamber and configured to measure an amount of UV radiation.

74. An air pressure control system according to claim 73, wherein the UV sensor is in communication with the microprocessor such that the microprocessor can control the fan speed based on a signal transmitted by the UV sensor.

75. An air-pressure-control system according to claim 64, further comprising a first filter located within the airflow.

76. An air pressure control system according to claim 75, wherein the system includes a second filter located at a second end of the germicidal radiation chamber.

77. An air pressure control system according to claim 64, the system further comprising a cover having a closed position and an open position, the cover configured to close the system inlet when the system is not in use, thereby preventing airflow through the system.

78. An air pressure control system according to claim 77, the system further comprising an interlock switch connected to the cover and configured to sense a position of the cover and prevent system operation if the cover is in the closed position.

79. An air-pressure-control system, the system comprising:
   a system inlet;
   a system outlet;
   a variable-speed fan configured to operate at a speed;
   a motor controller in communication with the fan and configured to control the speed of the fan;
   a solid state anemometer configured to monitor an air pressure differential between the system inlet and the system outlet; and
   a closed-loop controller in communication with the motor controller and the solid state anemometer, wherein the closed-loop controller is configured to vary the speed of the fan based on the pressure differential between the inlet and outlet of the system, thereby controlling a pressure within a space, the closed-loop controller bringing the fan to full speed upon a change in condition within the space, the closed-loop controller then reducing the speed of the fan to obtain a setpoint value.

80. An air-pressure-control system according to claim 79, wherein the closed-loop controller includes:
   a microprocessor configured to compare an output from the solid state anemometer and the setpoint value and adjust the speed of the fan based on the difference between the solid state anemometer output and the setpoint value.

81. An air-pressure-control system according to claim 80, further comprising a safety sensor in communication with the microprocessor, the microprocessor configured to alarm when the air-pressure-control system is not operating at the setpoint values.

82. An air-pressure-control system according to claim 80, further comprising:
   a germicidal radiation chamber located within an airflow path in the air-pressure-control system, wherein the germicidal radiation chamber includes at least one UV light source.

83. An air-pressure-control system according to claim 82, wherein the germicidal radiation chamber further includes a reflective interior surface configured to reflect UV light produced by the UV light source.

84. An air-pressure-control system according to claim 82, wherein an input and exit of the airflow path are blackened to prevent UV reflection through the system inlet and system outlet.

85. An air-pressure-control system according to claim 82, wherein the germicidal radiation chamber is a removable cartridge.

86. An air-pressure-control system according to claim 82, wherein the microprocessor controls the operation of the at least one UV light source.

87. An air-pressure-control system according to claim 82, further comprising at least one baffle located at an least one end of the germicidal radiation chamber, wherein the at least one baffle is configured to prevent UV light from exiting the germicidal radiation chamber.

88. An air-pressure-control system according to claim 87, wherein at least a portion of an edge of the at least one baffle is in contact with the germicidal radiation chamber.

89. An air-pressure-control system according to claim 87, wherein the at least one baffle straightens the air flow through the system.

90. An air-pressure control system according to claim 89, wherein the baffles have a reflective surface facing the germicidal radiation chamber and configured to reflect UV light produced by the UV light source.

91. An air pressure control system according to claim 82, the system further including an air flow sensor located within the germicidal radiation chamber.

92. An air pressure control system according to claim 91, wherein the air flow sensor is oriented such that it is co-linear with a flow of air through the system.

93. An air pressure control system according to claim 91, wherein the air flow sensor is a solid state sensor.

94. An air pressure control system according to claim 91, wherein the air flow sensor is in communication with the microprocessor such that the microprocessor can control the fan speed based on a signal transmitted by the air flow sensor.

95. An air pressure control system according to claim 82, the system further comprising a UV sensor located within the germicidal radiation chamber and configured to measure an amount of UV radiation.

96. An air pressure control system according to claim 95, wherein the UV sensor is located in the air flow path.

97. An air pressure control system according to claim 95, wherein the UV sensor is in communication with the microprocessor such that the microprocessor can control the fan speed based on a signal transmitted by the UV sensor.

98. An air-pressure-control system according to claim 82, wherein the air-pressure-control system is configured for through-window installation.

99. An air-pressure-control system according to claim 82, further comprising a first filter located within the airflow.

100. An air-pressure-control system according to claim 99, wherein the first filter is a HEPA filter.

101. An air-pressure-control system according to claim 99, wherein the germicidal radiation chamber has at least one slot providing access to the filter.

102. An air-pressure-control system according to claim 99, wherein the first filter is located at a first end of the germicidal radiation chamber.

103. An air-pressure control system according to claim 102, wherein the system includes a second filter located at a second end of the germicidal radiation chamber.

104. An air-pressure control system according to claim 99, wherein the first filter is translucent.

105. An air-pressure control system according to claim 99, wherein the first filter has a metal frame.

106. An air-pressure control system according to claim 105, wherein at least a portion of the metal frame contacts the germicidal radiation chamber.

107. An air-pressure control system according to claim 99, wherein the first filter is pleated.

108. An air-pressure control system according to claim 107, wherein the first filter is oriented such that the pleats are oriented vertically.

109. An air-pressure control system according to claim 107, wherein the at least one UV light source is oriented such that it is transverse to the pleats of the first filter.

110. An air pressure control system according to claim 79, the system further comprising a cover having a closed and open position configured to close the system inlet when the system is not in use, thereby preventing airflow through the system.

111. An air pressure control system according to claim 110, wherein the cover is made from insulating material.

112. An air pressure control system according to claim 110, the system further comprising an interlock switch connected to the cover and configured to sense a position of the cover and prevent system operation if the cover is in the closed position.

113. An air pressure control system according to claim 112, the system further comprising:
a germicidal radiation chamber located within an airflow path in the air-pressure-control system, wherein the germicidal radiation chamber includes at least one UV light source, wherein the interlock switch is connected to a microprocessor.

114. An air pressure control system according to claim 79, wherein the closed-loop controller includes a software port for downloading new software to the system.

115. An air pressure control system according to claim 42, wherein the differential-air-pressure transducer is heated.

116. An air pressure control system according to claim 42, further comprising at least one filter in the second air flow path.

117. An air pressure control system according to claim 59, wherein at least a portion of the metal frame is in contact with the germicidal radiation chamber.

* * * * *